United States Patent [19]

Kraatz et al.

[11] Patent Number: 4,614,828

[45] Date of Patent: Sep. 30, 1986

[54] TRICHLOROMETHYLPHOSPHONODITHI-OATES

[75] Inventors: Gary W. Kraatz, San Jose; Charles G. Chavdarian, Martinez; Valerie F. Heusinkveld, Berkeley, all of Calif.

[73] Assignee: Stauffer Chemical Co., Westport, Conn.

[21] Appl. No.: 649,037

[22] Filed: Sep. 10, 1984

[51] Int. Cl.$^4$ .............................................. C07F 9/40
[52] U.S. Cl. ........................................ 558/203; 71/87
[58] Field of Search ................. 260/961, 986; 558/203

[56] References Cited

U.S. PATENT DOCUMENTS 4,472,390  9/1984  Fahmy .............................. 260/961

Primary Examiner—Anton H. Sutto
Attorney, Agent, or Firm—Harry A. Pacini; Leona L. Lauder

[57] ABSTRACT

Herbicidally active thiocarbamates are employed in combination with certain mono-, di- or trihaloalkyl-phosphonodithioates, the latter in sufficient quantity to lessen the rate of soil degradation of the former. As a result, the herbicidal, effectiveness of the thiocarbamate is significantly enhanced and prolonged, rendering a single application or multiple applications of the herbicide effective over a longer period of time. Such herbicidal compositions can optionally contain a non-phytotoxic antidotally effective amount of an amide of haloalkanoic or dihaloalkanoic acid. Also novel compounds trichloro- and bromodichloro- methylphosphonodithioates and the process for their preparation are disclosed.

2 Claims, No Drawings

TRICHLOROMETHYLPHOSPHONODITHIO-ATES

BACKGROUND OF THE INVENTION

This invention relates to herbicidal compositions and methods of use. In particular, this invention relates to herbicidal compositions comprising an herbicidally active thiocarbamate in combination with certain mono-, di- and tri-haloalkylphosphonodithioates, the latter serving to prolong the effectiveness of a single application or multiple applications of the thiocarbamate herbicide in controlling undesired plant growth.

Thiocarbamates are well known in the agricultural art as herbicides useful for weed control in crops such as corn, potatoes, beans, beets, spinach, tobacco, tomatoes, alfalfa, and others. Thiocarbamates are primarily used in pre-emergence application. They have been found to be particularly effective when incorporated into the soil prior to the planting of the crop. As a herbicide, the thiocarbamate is most concentrated immediately after its application. How long thereafter the initial concentration is retained depends in large part on the particular soil used. Thus the rate at which the thiocarbamate herbicide concentration declines following its application tends to vary from one type of soil to the next. This is evident in the observable extent of actual weed control after considerable time has elapsed.

It has now been discovered that the soil persistence of certain herbicidally active thiocarbamates is significantly extended by the incorporation of certain mono-, di- and tri-haloalkylphosphonodithioate compounds, which have insignificant or no herbicidal activity of their own at the rates and under the conditions applied. This improvement in the soil persistence of the thiocarbamate can manifest itself in a variety of ways. Improved soil persistence can be shown by herbicidal efficacy tests, wherein the degree of weed injury is measured after a set period of time following application of the herbicide. In such a test, the extender compound is shown to increase the herbicidal effectiveness of the thiocarbamate by increasing the persistence of the latter in the soil, and thus prolonging its effective life.

It is therefore an object of this invention to increase the soil persistence of thiocarbamate herbicides and thus improve their herbicidal effectiveness.

In particular, this invention relates to a novel herbicidal composition comprising (a) an herbicidally effective amount of a thiocarbamate having the formula

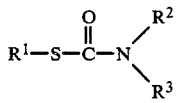

$R^1$ is $C_1$–$C_6$ alkyl, $C_3$–$C_6$ alkenyl, $C_7$–$C_9$ phenylalkyl, or phenyl and is optionally substituted with one, two, or three halogen atoms, and $R^2$ and $R^3$ are either selected independently from $C_1$–$C_6$ alkyl and $C_5$–$C_7$ cycloalkyl, or combined to form conjointly $C_4$–$C_7$ alkylene;

(b) a non-herbicidal extending amount of a mono-, di- or tri-haloalkylphosphonodithioate compound sufficient to extend the soil life of said thiocarbamate, said extender compound having the formula

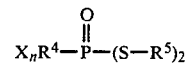

in which
X is halo;
n is 1, 2 or 3;
$R^4$ is $C_1$–$C_4$ alkyl; and
$R^5$ is $C_1$–$C_6$ alkyl or $C_2$–$C_4$ alkenyl.

In a preferred embodiment of the invention, the compounds above are defined such that
$R^1$ is $C_1$–$C_6$ alkyl, $C_7$–$C_9$ phenylalkyl or phenyl;
$R^2$ and $R^3$ are either selected independently from $C_1$–$C_6$ alkyl and $C_5$–$C_7$ cycloalkyl or combined to form conjointly $C_4$–$C_7$ alkylene;
X is chloro;
n is 1, 2 or 3;
$R^4$ is methyl or ethyl; and
$R^5$ is n-propyl, n-butyl or allyl.

In another preferred embodiment of the invention,
$R^1$ and $R^2$ are each independently $C_1$–$C_6$ alkyl;
$R^3$ is $C_1$–$C_6$ alkyl or $C_5$–$C_7$ cycloalkyl;
X is chloro;
n is 1, 2 or 3;
$R_4$ is methyl; and
$R_5$ is n-propyl or n-butyl.

In still another preferred embodiment,
$R^1$, $R^2$ and $R^3$ are each independently $C_2$–$C_4$ alkyl;
X is chloro;
n is 2 or 3;
$R^4$ is methyl; and
$R^5$ is n-propyl or n-butyl.

This invention further relates to a method of controlling undesirable vegetation comprising applying the above composition to the locus where control is desired.

The invention further relates to new compounds having the formula

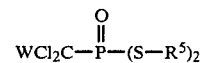

in which W is chlorine or bromine and $R^5$ is $C_1$–$C_6$ alkyl or $C_2$–$C_4$ alkenyl. $R^5$ is preferably n-propyl, n-butyl or allyl. W is most preferably chlorine.

The invention further relates to a process for preparing the above-disclosed novel compounds. Such process is described below after Example 1.

The terms "alkyl" and "alkenyl" are used herein, unless otherwise specified, in their normal meanings and are intended to include both straight-chain and branched-chain groups.

All carbon atom ranges are intended to be inclusive of their upper and lower limits.

The terms "halogen atom" or "halo" are used to designate fluorine, chlorine, bromine, or iodine atoms, as well as any combination thereof.

The term "herbicide," as used herein, means a compound which adversely controls or modifies the growth of plants. By the term "herbicidally effective amount" is meant an amount of compound which causes an adverse modifying effect upon the growth of plants. By "plants" is meant germinant seeds, emerging seedlings and established vegetation, including roots and above-ground portions. Such adverse controlling or modifying effects include all deviations from natural development, for example, killing, retardation, defoliation, desiccation, regulation, stunting, tillering, stimulation, leaf burn, dwarfing and the like.

The term "non-herbicidal" as used herein means that the extender compound at the rate and in the manner applied has insignificant or no herbicidal activity of its own.

The term "extending amount" describes the amount of extender sufficient to prolong the soil life of the thiocarbamate herbicide.

The phrase "to extend the soil life and said thiocarbamate" is used herein to denote the effect whereby herbicidal effectiveness of the thiocarbamate is maintained over time. An extended soil life can be manifested by a slower rate of decline of weed killing potency.

DETAILED DESCRIPTION OF THE INVENTION

The herbicidally active thiocarbamates within the scope of the present invention can be prepared by the process described in U.S. Pat. No. 2,913,327 (Tilles et al., Nov. 17, 1959).

The mono- and dihaloalkylphosphonodithioate compounds of this invention may be prepared in general by a one-step process indicated by the following representative reaction:

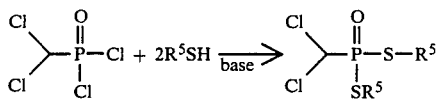

The dichloromethylphosphonyl dichloride is reacted with two equivalents of an appropriately substituted mercaptan in the presence of a base. The dichloromethylphosphonyl dichloride, a representative starting material, may be obtained by the procedure described in A. M. Kinnear and E. A. Perren, "Formation of Organo-phosphorus Compounds by the Reaction of Alkyl Chlorides with Phosphorous Trichloride in the Presence of Aluminum Chloride," *Journal of the Chemical Society*, 1952, pp. 3437–45.

The reaction is advantageously carried out at a temperature of from about 20° C. to about 110° C. in an organic solvent in the presence of a base, particularly a tertiary amine. Suitable solvents include aromatic hydrocarbons such as benzene or toluene, ethers such as diethyl ether or tetrahydrofuran, nitriles such as acetonitriles, and ketones such as acetone. Suitable tertiary amines include triethylamine, dimethylaniline, diethylaniline, and pyridine. Inorganic bases such as sodium or potassium cabonate may also be used. As the reaction is exothermic, the base is preferably added dropwise when operating on the laboratory scale. The product may be recovered by evaporating or distilling off the solvent, and purification by either chromatography or distillation.

The following is an example of the preparation of compounds of this invention.

EXAMPLE 1

Preparation of S,S-Di-n-Propyl Dichloromethylphosphonodithioate

To a solution of 11.0 grams (g) (0.0545 mole) of dichloromethylphosphonyl dichloride in 250 milliliters (ml) of toluene, maintained under nitrogen and at room temperature, was added 10.84 ml (0.12 mole) of 1-propanethiol. To this solution was added dropwise a solution of 18.22 ml (0.131 mole) of triethylamine in 35 ml of toluene. The resultant mixture was refluxed for 30 minutes. After cooling, the mixture was filtered (using an aspirator), and the solution was then evaporated to a mobile oil. Bulb-to-bulb distillation [oven temperature 100°–120° C. (0.2 torr)] yielded 12.67 g (83%) of the title compound, as a clear, mobile oil. The structure was confirmed by nuclear magnetic resonance, mass and infrared spectroscopy.

The trihalomethylphosphonodithioate compounds of this invention can be prepared by halogenating the appropriate S,S-alkyl or alkenyl substituted dichloromethylphosphonodithioate with a suitable halogenating agent in the presence of an appropriate non-nucleating base. A preferred base is lithium diisopropylamide. Other preferred bases include lithium dialkylamides, such as lithium diethylamide, lithium dicyclohexylamide, and lithium isopropylcyclohexylamide; and lithium diarylamides, such as lithium diphenylamide and lithium 2,2,6,6-tetramethylpiperidide. Other preferred bases include other alkali metal, such as potassium and sodium, non-nucleophilic amides. Nucleophilic bases such as n-butyllithium or lithium dimethylamide are too reactive for the purpose. Other preferred bases are alkali metal trialkylmethides wherein each alkyl group has at least two carbon atoms, such as lithium triethyl, tri-n-propyl, triisoporpyl, tri-n-butyl and tri-t-butyl methides, which group includes alkali metal tricycloalkyl methides, such as tricyclohexylmethide, and also triaryl alkali methides, such as lithium triphenylmethide.

An excess of base is employed. The base may be formed in situ as shown in Example 2 wherein n-butyl lithium is reacted with diisopropylamine to form lithium diisopropylamide or the bases may be obtained commercially, as from for example, Alfa Chemical Company.

The base is reacted with the appropriately substituted phosphonodithioate before the halogenating agent, preferably a chlorinating or a brominating agent is added to the reaction mixture.

Carbon tetrachloride is a preferred chlorinating agent. Another preferred chlorinating agent is hexachloroethane. Brominating agents include carbon tetrabromide, bromotrichloromethane, ethylene dibromide and diethyl dibromomalonate. Other completely chlorinated or brominated saturated aliphatic hydrocarbons can be employed.

The temperature range for optionally forming the non-nucleophilic organometallic base from about −78° C. to about −10° C. A preferred temperature range is from about −30° C. to −20° C.

The temperature range for reacting said base with the appropriately substituted phosphonodithioate and for chlorinating the phosphonodithioate product of said reaction is from about −100° C. to about −40° C., and more preferably from about −80° C. to about −60° C. The most preferred range is from about −78° C. to about −62° C.

Ethereal solvents, such as tetrahydrofuran, diethyl ether or 1,2-dimethoxy ethane can be used in these reactions.

Conventional extraction techniques are used to yield the desired product.

Example 2 shows in detail a representative preparation of such a trihaloalkylphosphonodithioate compound.

EXAMPLE 2

Preparation of S,S-Di-n-propyl Trichloromethylphosphonodithioate

To a solution of 0.42 g (0.0047 mole) of diisopropylamine in 10 ml tetrahydrofuran (THF), maintained under inert gas and cooled to −25° C., was added dropwise a solution of n-butyllithium (0.043 mole) in hexane such that the temperature did not exceed −20° C. The solution was stirred at −35° C. for 30 minutes, then cooled to −65° C. A solution of 1.1 g (0.004 mole) of S,S-di-n-propyl dichloromethylphosphonodithioate in 20 ml THF was added dropwise over 20 minutes. After stirring at −65° C. for 60 minutes, a solution of 0.62 g (0.004 mole) of carbon tetrachloride in 10 ml THF was added over 10 minutes. The solution was stirred at −65° C. for 60 minutes, then allowed to warm to room temperature. After cooling in an ice bath, 25 ml of water was added. The reaction mixture was extracted with dichloromethane (2×40 ml) and the combined organic extracts were washed with saturated sodium bicarbonate (2×20 ml), and dried with magnesium sulfate. Evaporation afforded a red oil, the title compound. The structure Tas confirmed by nuclear magnetic resonance and mass spectroscopy.

Compounds which can be prepared by the above reactions or by reactions analogous thereto, and which have been found to act as extenders for thiocarbamates are listed by structure in the following Table of Compounds.

TABLE 1
TABLE OF COMPOUNDS $$X_n R^4 - \overset{\overset{O}{\|}}{P} - (S-R^5)_2$$

| Compound Number | $X_n R^4$ | $R^5$ |
|---|---|---|
| 1 | $Cl_2CH-$ | $n\text{-}C_3H_7$ |
| 2 | $Cl_2CH-$ | $sec\text{-}C_4H_9$ |
| 3 | $Cl_2CH-$ | $-C_2H_5$ |
| 4 | $Cl_2CH-$ | $-n\text{-}C_4H_9$ |
| 5 | $Cl_2CH-$ | $-n\text{-}C_5H_{11}$ |
| 6 | $Cl_2CH-$ | $-iso\text{-}C_4H_9$ |
| 7 | $Cl_2CH-$ | $-allyl$ |
| 8 | $Cl_2CH-$ | $-methallyl$ |
| 9 | $ClCH_2-$ | $n\text{-}C_3H_7$ |
| 10 | $ClCH_2CH_2-$ | $n\text{-}C_3H_7$ |
| 11 | $Cl_3C-$ | $n\text{-}C_3H_7$ |

The objects of the present invention are achieved by applying the thiocarbamate extender compound to the soil at an agricultural field site in conjunction with the thiocarbamate herbicide. The two compounds can be applied simultaneously in a single mixture or in separate formulations, or they can be applied in succession, with either one following the other. In successive application, it is preferable to add the compounds as close in time as possible.

The herbicide extending effect is operable over a wide range of weight ratios of the two compounds. It is most convenient, however, to apply the compounds at a weight ratio of about 0.2:1 to about 30:1 (herbicide/extender), preferably about 0.5:1 to about 20:1, and most preferably about 0.5:1 to about 12:1.

Thiocarbamate herbicides useful in the present invention include those disclosed in U.S. Pat. No. 2,913,327, and preferably include S-ethyl N,N-di-n-propylthiocarbamate; S-ethyl N,N-diisobutylthiocarbamate; S-n-propyl N,N-di-n-propylthiocarbamate; and S-n-propyl ethyl-n-butyl thiocarbamate; S-ethyl-N-ethyl-N-cyclohexylthiocarbamate; S-ethyl hexahydro-1H-azepine-1-carbothioate; S-benzyl N,N-di-n-propylthiocarbamate; and S-benzyl N-ethyl-N-1,2-dimethylpropylthiocarbamate.

Specific dichloromethylphosphonodithioate extenders which have been found to be effective in the compositions of the present invention include S,S-di-n-propyl dichloromethylphosphonodithioate, S,S-di-n-butyl dichloromethylphosphonodithioate, S,S-di-allyl dichloromethylphosphonodithioate, S,S-di-sec-butyl dichloromethylphosphonodithioate, and S,S-di-n-pentyl dichloromethylphosphonodithioate. Other symmetrically substituted monohaloalkyl phosphonodithioates found to be effective thiocarbamate extenders include S,S-di-n-propyl 2-chloroethylphosphonodithioate and S,S-di-n-propyl chloromethylphosphonodithioate.

ANTIDOTES

The variety of crops on which the present composition is useful can be significantly broadened by the use of an antidote to protect the crop from injury and render the composition more selective against weeds.

For antidote descriptions and methods of use, reference is made to U.S. Pat. No. 3,959,304, issued to Teach on May 25, 1976; U.S. Pat. No. 3,989,503, issued to Pallos et al. on Nov. 2, 1976; U.S. Pat. No. 4,021,224, issued to Pallos et al. on May 3, 1977; U.S. Pat. No. 3,131,509, issued to Hoffman on May 5, 1964; U.S. Pat. No. 3,564,768, issued to Hoffman on Feb. 3, 1971; U.S. Pat. No. 4,137,070, issued to Pallos et al. on Jan. 30, 1979; U.S. Pat. No. 4,294,764, issued to Rinehart on Oct. 13, 1981; U.S. Pat. No. 4,256,481, issued to Gardi et al. on May 17, 1981; U.S. Pat. No. 4,415,353, issued to Pallos et al. on Nov. 15, 1983; and U.S. Pat. No. 4,415,352, issued to Pallos et al. on Nov. 15, 1983.

Useful antidotes include acetamides during the formula

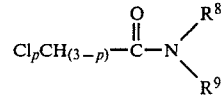

in which p is 1 or 2, and $R^8$ and $R^9$ are independently $C_1$-$C_{12}$ alkyl, $C_2$-$C_{12}$ alkenyl, $C_1$-$C_4$ alkylene substituted with phenyl, dialkoxyalkyl wherein the alkoxy and alkyl groups each have 1–4 carbon atoms, and $C_1$-$C_4$ alkylene substituted with a 5- to 8-membered heterocyclic ring.

Preferable embodiments of said antidotes include those wherein p is 1 or 2, $R^8$ and $R^9$ are independently $C_1$-$C_6$ alkyl, $C_2$-$C_6$ alkenyl, dialkoxyethyl, cyclic acetal or $C_1$-$C_2$ alkylene substituted with phenyl. Further preferred embodiments include those antidotes wherein p is 2, $R^8$ and $R^9$ are independently $C_1$-$C_4$ alkyl, $C_2$-$C_4$ alkenyl, dimethoxyethyl, dioxolanylmethyl or benzyl. Examples falling within the above formula are N,N-diallyl dichloroacetamide, N,N-diallyl chloroacetamide, N-allyl-N-2,2-dimethoxyethyl dichloroacetamide, N-allyl-N-[2-(1,3-dioxolanyl)]-methyl dichloroacetamide and 2,2-dichloro-N-ethyl-N-benzyl acetamide.

Further useful antidotes are oxazolidines and thiazolidines having the formula

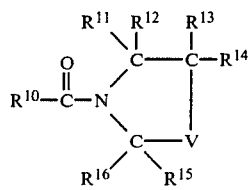

in which $R^{10}$ is $C_1$-$C_4$ alkyl, haloalkyl, or dihaloalkyl, $R^{11}$, $R^{12}$, $R^{13}$, $R^{15}$ and $R^{16}$ are each independently hydrogen or methyl, $R^{14}$ is hydrogen, methyl or phenyl, and V is oxygen or sulfur. Examples of such antidotes include 2,2,5-trimethyl-N-dichloroacetyl oxazolidine ($R^{10}$=CHCl$_2$, $R^{11}$=$R^{12}$=$R^{13}$=$R^{14}$=H; $R^{15}$=$R^{16}$=$R^{17}$=CH$_3$; V=O); 2,2-dimethyl-N-dichloroacetyl thiazolidine ($R^{10}$=CHCl$_2$; $R^{11}$=$R^{12}$=$R^{13}$=$R^{14}$=H; $R^{15}$=$R^{16}$=CH; V=S); and 2,2-dimethyl-3-dichloroacetyl-5-phenyl oxazolidine ($R^{11}$=$R^{12}$=$R^{13}$=H; $R^{14}$=phenyl; $R^{15}$=$R^{16}$=CH$_3$).

Further useful antidotes are dichloroacetamide derivatives having the formula

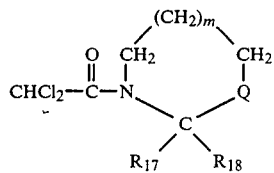

in which
Q is oxygen, sulfur, SO or SO$_2$;
m is 0 or 1, and
$R^{17}$ and $R^{18}$ are identical or different and represent hydrogen, alkyl or halophenyl, hydroxyl or nitro; or
$R^{17}$ and $R^{18}$ together form a butylene, pentylene or hexylene group which can be substituted with one or two methyl groups, with the proviso that if m=0, $R^{17}$ and $R^{18}$ are not hydrogen, alkyl or substituted phenyl.

A preferable embodiment of said antidotes include those wherein Q and m are defined as above and $R^{17}$ and $R^{18}$ together form an unsubstituted butylene, pentylene or hexylene ring, or a butylene, pentylene or hexylene ring substituted by 1 or 2 methyl groups. Examples of such antidotes include N-dichloroacetyl-1-oxa-5-azaspiro-(5,5)-undecane; N-dichloroacetyl-1-oxa-4-azaspiro-(4,5)-decane; N-dichloroacetyl-10-methyl-1-oxa-4-azaspiro-(4,5)-decane; N-dichloroacetyl-8-methyl-1-oxa-4-azaspiro-(4,5)-decane; N-dichloroacetyl-6,10-dimethyl-1-oxa-4-azaspiro-(4,5)-decane; N-dichloroacetyl-1-thia-4-azaspiro-(4,5)-decane; N-dichloroacetyl-1-oxa-5-azaspiro-(5,6)-dodecane; and N-dichloroacetyl-1-oxa-4-azaspiro-(4,4)-nonane.

A still further useful antidote is 1,8-naphthalic anhydride.

The antidote is applied in conjunction with the thiocarbamate and the mono- and dihaloalkylphosphonodithioate extender in a non-phytotoxic antidotally effective amount. By "non-phytotoxic" is meant an amount of the antidote which causes at most minor injury to the desired crop species. By "antidotally effective" is meant an amount of the antidote which substantially decreases the extent of injury caused by the thiocarbamate to the desired crop species. The preferred weight ratio of herbicide to antidote is from about 0.1:1 to about 40:1. The most preferred weight ratio range is from about 3:1 to about 25:1.

The following examples are offered to illustrate the compositions, methods, and effectiveness of the present invention, and are not intended to limit the invention in any way.

EXAMPLE 3

Herbicidal Activity Improvement Tests

This example offers herbicidal activity test data for a representative extender compound within the scope of this invention showing their effectiveness in improving the herbicidal activity of thiocarbamate herbicides. The effect is observed by comparing the extent of weed control in test flats treated with a thiocarbamate herbicide against that occurring in similar flats treated with both the thiocarbamate herbicide and a mono- and dihaloalkylphosphonodithioate extender. The soil used in these tests was a sandy loam soil from Sunol, Calif., which was pretreated with the herbicide to simulate a typical field which had received previous herbicide applications.

The following thiocarbamate herbicides were employed in these tests:
SUTAN®=S-ethyl-N,N-di-isobutyl thiocarbamate; and
EPTAM®=S-ethyl N,N-di-n-propyl thiocarbamate.

A. Soil Pre-Treatment

The soil was pre-treated with EPTAM® for herbicidal activity improvement tests with EPTAM® or antidoted EPTAM®. Similarly, the soil was pretreated with SUTAN® for later tests with SUTAN®, antidoted or unantidoted.

Stock solutions were prepared by diluting an emulsifiable liquid concentrate containing 6 lb/gal (0.72 kg/l) (76.8% by weight) of the herbicide EPTAM® or of the herbicide SUTAN® (77.3% by weight) in 200 ml of water, such that the resulting concentration of herbicide in the solution was 2000 mg/l. Two hundred ml of each of the solutions was then added to different 200 lb (90.8 kg) batches of soil to which 17-17-17 fertilizer (N-P$_2$O$_5$-K$_2$O on a weight basis) had been previously added to a concentration of 50 ppm by weight with respect to the soil. The batches of soil were then individually mixed in a rotary mixer for 10 to 30 minutes. The rate applied was equivalent to 3 lb/acre.

The soil was then placed in round plastic containers, 7.5 inches (19.0 cm) in diameter by 7.5 inches (19.0 cm) deep. The soil was tamped and leveled with a row marker to impress one row across the width of each container. This row was sealed with watergrass (*Echinochloa crus-galli*). Sufficient seeds were planted to produce several seedlings. The containers were then placed in a greenhouse maintained at 20° C. to 30° C. and watered daily by sprinkler.

About six weeks after treatment, the soil was allowed to dry out and the plant foliage was removed. The soil was then passed through a 0.25 inch (0.64 cm) screen to remove plant roots and clods.

B. Herbicide Test

Stock solutions were then prepared by diluting either an emulsifiable liquid concentrate containing 6 lb/gal (0.72 kg/l) (76.8% by weight) of the herbicide EPTAM® or of the herbicide SUTAN® (77.3% by weight) in 675 ml of water such that the resulting concentration of herbicide in the solution was 1.14 mg/ml. Five ml of either solution when added to three pounds of soil yielded a quantity in the soil equivalent to three pounds per acre.

The extender compounds were used in technical form. Each representative extender was dissolved in 5 ml acetone and 14.5 ml water such that the resulting concentration of the extender in the solution was 1.54 mg/ml. Five ml of this solution when added to three pounds of soil yielded a quantity in the soil equivalent to four periods per acre.

Five ml of an extender solution and 5 ml of a herbicide solution were tank-mixed. The resultant mixture of 10 ml was then added to 3 lbs of soil and incorporated into the appropriately pre-treated soil by a rotary mixer. Thus, 10 ml of the mixture and 3 pounds of soil were placed in rotary mixer and incorporated, yielding a quantity of herbicide and extender in the soil of 3 and 4 lb/A, respectively.

The treated soil was then placed in aluminum flats which were approximately 3.5 inches deep, 7.5 inches wide, and 2.5 inches long (8.9×19.5×6.4 cm). The soil was tamped and leveled with a row marker to impress six rows across the width of the flat. The test weeds were as follows:

| COMMON NAME | ABBREVIATION | SCIENTIFIC NAME |
|---|---|---|
| watergrass | WG | *Echinochloa crus-galli* (L.) |
| wild oats | WO | *Avena fatua* (L.) |
| shattercane | SHC | *Sorghum bicolor* (L.) Moench |

R-10 milo (*Sorghum bicolor*) was also used as a plant growth indicator. Two rows of watergrass were planted.

One row of DeKalb XL-25A corn of species *Zea mays* (L.) was also planted.

Sufficient seeds were planted to produce several seedlings. The flats were then placed in a greenhouse maintained at 70° to 85° F. (21° to 30° C.) and watered daily by sprinkler.

Approximately three weeks after treatment, the degree of weed control and corn injury was estimated and recorded as a percentage compared to the growth of the same species in a check flat of the same age which had been seeded in conditioned soil but not treated with either an herbicide or an extender. The rating scale ranges from 0 to 100%, where 0 equals no effect with plant growth equal to the untreated check, and 100 equals complete kill.

The results are listed in Table 2. The average percentage of weed control in the last column is the average for the above-identified weed species and plant growth indicator. There was no injury to the corn. Control experiments (herbicide alone with no extender present) were included in the batch for comparison. Substantial improvement in average percent weed control over the control experiments is evident when an extender was present. The herbicidal efficacy of the thiocarbamate three weeks after application was much improved by the use of the extender, whereas the corn remained unaffected.

An asterisk (*) means the percentage is an average of two trials run at the same time. A double asterisk (**) means the percentage is the average of four trials run at the same time.

TABLE 2

HERBICIDAL ACTIVITY

Herbicide: S—ethyl N,N—di-n-propyl thiocarbamate and S—ethyl N,N—diisobutyl thiocarbamate
Extender: As Keyed to Table I by Compound No.
Application Rate: Herbicide 3 lb/A - Extender 4 lb/A
Rating Time: Three weeks after second treatment

| Treatment | | Average % |
|---|---|---|
| Herbicide | Extender No. | Weed Control |
| EPTAM | — | 6* |
| EPTAM | 1 | 91 |
| EPTAM | — | 3* |
| EPTAM | 2 | 25 |
| EPTAM | — | 4* |
| EPTAM | 3 | 9 |
| EPTAM | — | 4* |
| EPTAM | 4 | 86 |
| EPTAM | — | 4* |
| EPTAM | 5 | 25 |
| EPTAM | — | 4* |
| EPTAM | 6 | 20 |
| EPTAM | — | 4* |
| EPTAM | 7 | 36 |
| EPTAM | — | 4* |
| EPTAM | 8 | 16 |
| EPTAM | — | 21* |
| EPTAM | 11 | 97 |

*Average of two trials.

EXAMPLE 4

Bioassay Extender Tests at Different Rates

The same procedures as used in Example 3 [(A) Soil Pre-Treatment and (B) Herbicide Test] were employed in this example except that the extenders were applied at varying rates. The same procedure to prepare stock solutions was employed as in Example 3. The appropriate ml of the extender solution were tank-mixed with 5 ml of the herbicide stock solution to yield the desired application rates.

The ratings, approximately three weeks after the second treatment with the herbicidal compositions, were taken under the criteria of Example 3, Part (B). In each instance, a dramatic improvement over the herbicide alone in pre-treated soil was observed.

TABLE 3

HERBICIDAL ACTIVITY

Herbicide: S—ethyl N,N—di-n-propyl thiocarbamate and S—ethyl N,N—diisobutyl thiocarbamate both applied at 3 lb/A
Herbicide Application Rate: Constant at 3 lb/Acre
Extender: Keyed to Table 1 by Compound No.
Rating Time: Three weeks after treatment

| Treatment | | Extender | Average % |
|---|---|---|---|
| Herbicide | Extender No. | Application Rate | Weed Control |
| EPTAM | — | — | 4* |
| EPTAM | 1 | 0.5 | 17 |
| EPTAM | 1 | 1.0 | 37 |
| EPTAM | 1 | 2.0 | 75 |
| EPTAM | 1 | 4.0 | 88 |
| EPTAM | — | — | 4* |
| EPTAM | 1 | 0.5 | 27 |
| EPTAM | 1 | 1.0 | 57 |
| EPTAM | 1 | 2.0 | 75 |
| EPTAM | 1 | 4.0 | 95 |
| EPTAM | — | — | 3* |
| EPTAM | 1 | 0.5 | 7 |
| EPTAM | 1 | 1.0 | 37 |
| EPTAM | 1 | 2.0 | 71 |
| EPTAM | 1 | 4.0 | 92 |
| EPTAM | — | — | 3* |
| EPTAM | 1 | 0.5 | 10 |

TABLE 3-continued

HERBICIDAL ACTIVITY

Herbicide: S—ethyl N,N—di-n-propyl thiocarbamate and S—ethyl N,N—diisobutyl thiocarbamate both applied at 3 lb/A
Herbicide Application Rate: Constant at 3 lb/Acre
Extender: Keyed to Table 1 by Compound No.
Rating Time: Three weeks after treatment

| Treatment Herbicide | Extender No. | Extender Application Rate | Average % Weed Control |
|---|---|---|---|
| EPTAM | 1 | 1.0 | 21 |
| EPTAM | 1 | 2.0 | 45 |
| EPTAM | 1 | 4.0 | 84 |
| SUTAN | — | — | 0* |
| SUTAN | 1 | 0.5 | 6 |
| SUTAN | 1 | 1.0 | 32 |
| SUTAN | 1 | 2.0 | 64 |
| SUTAN | 1 | 4.0 | 77 |
| EPTAM | — | — | 3* |
| EPTAM | 2 | 0.5 | 2 |
| EPTAM | 2 | 1.0 | 9 |
| EPTAM | 2 | 2.0 | 11 |
| EPTAM | 2 | 4.0 | 25 |
| EPTAM | — | — | 3* |
| EPTAM | 3 | 0.5 | 2 |
| EPTAM | 3 | 1.0 | 5 |
| EPTAM | 3 | 2.0 | 10 |
| EPTAM | 3 | 4.0 | 20 |
| EPTAM | — | — | 3* |
| EPTAM | 4 | 0.5 | 10 |
| EPTAM | 4 | 1.0 | 21 |
| EPTAM | 4 | 2.0 | 53 |
| EPTAM | 4 | 4.0 | 75 |

*Average of two trials.

EXAMPLE 5

Herbicidal Activity of 3-Component Compositions

This example, as Examples 3 and 4 above, offers evidence of the effectiveness of representative extenders of this invention in prolonging thiocarbamate herbicides' ability to control weeds by comparing at a set period after application the weed injury caused by two-component compositions, that is, comprising a thiocarbamate and an antidote to that caused by three-component compositions comprising a thiocarbamate herbicide, an antidote and an extender.

Essentially the same procedures were followed for the tests in this example as described in Example 3, above except that an antidote was employed in the compositions tested. The same procedure as in Example 3(A) was followed for soil pre-treatment, except that an antidote was employed in the composition used for pre-treatment.

Stock solutions containing either the thiocarbamate SUTAN® or EPTAM® each with an amide of a dihaloalkanoic acid were prepared as follows:

An emulsifiable liquid concentrate of EPTAM® (82.8%) and of N,N-diallyl-dichloroacetamide (6.9%) or of SUTAN® (85.2%) and N,N-diallyl dichloroacetamide (3.5%) was diluted in water such that the resulting concentration of herbicide in each of the solutions was 1.14 mg/ml. The weight ratio of EPTAM® to the antidote was 12:1 whereas the weight ratio of SUTAN® to the antidote is 24:1.

Appropriate amounts of the stock solutions of each of the representative extenders were applied to yield the desired application rate. The rest of the procedure of Example 2(B) including the evaluation criteria was followed. The results were recorded in Table 4. An asterisk (*) indicates that the percentage is an average of two trials whereas a double asterisk (**) indicates an average of four trials.

TABLE 4

Herbicidal Activity
Herbicide: S—ethyl-N,N—di-n-propyl thiocarbamate or S—ethyl N,N—diisobutyl thiocarbamate
Herbicide Application Rate: Constant at 3 lb/Acre
Antidote: N,N—diallyl-dichloroacetamide
Extender: Keyed to Table I by Compound No.
Rating Time: Three weeks after treatment

| Treatment Herbicide | Antidote Application Rate | Extender Compound No. | Extender Application Rate | Average % Weed Control |
|---|---|---|---|---|
| EPTAM | 0.25 | — | — | 2** |
| EPTAM | 0.25 | 1 | 0.5 | 7 |
| EPTAM | 0.25 | 1 | 1.0 | 17 |
| EPTAM | 0.25 | 1 | 2.0 | 58 |
| EPTAM | 0.25 | 1 | 4.0 | 85 |
| EPTAM | 0.25 | — | — | 4* |
| EPTAM | 0.25 | 1 | 0.5 | 12 |
| EPTAM | 0.25 | 1 | 1.0 | 27 |
| EPTAM | 0.25 | 1 | 2.0 | 49 |
| EPTAM | 0.25 | 1 | 4.0 | 89 |
| SUTAN | 0.125 | — | — | 16** |
| SUTAN | 0.125 | 1 | 0.5 | 60 |
| SUTAN | 0.125 | 1 | 1.0 | 66 |
| SUTAN | 0.125 | 1 | 2.0 | 85 |
| SUTAN | 0.125 | 1 | 4.0 | 92 |
| EPTAM | 0.25 | — | — | 2** |
| EPTAM | 0.25 | 4 | 0.5 | 4 |
| EPTAM | 0.25 | 4 | 1.0 | 16 |
| EPTAM | 0.25 | 4 | 2.0 | 54 |
| EPTAM | 0.25 | 4 | 4.0 | 79 |
| EPTAM | 0.25 | — | — | 2* |
| EPTAM | 0.25 | 4 | 0.5 | 0 |
| EPTAM | 0.25 | 4 | 1.0 | 15 |
| EPTAM | 0.25 | 4 | 2.0 | 56 |
| EPTAM | 0.25 | 4 | 4.0 | 74 |
| SUTAN | 0.125 | — | — | 16** |
| SUTAN | 0.125 | 4 | 0.5 | 49 |
| SUTAN | 0.125 | 4 | 1.0 | 66 |
| SUTAN | 0.125 | 4 | 2.0 | 76 |
| SUTAN | 0.125 | 4 | 4.0 | 88 |
| SUTAN | 0.125 | — | — | 16** |
| SUTAN | 0.125 | 9 | 0.5 | 36 |
| SUTAN | 0.125 | 9 | 1.0 | 47 |
| SUTAN | 0.125 | 9 | 2.0 | 61 |
| SUTAN | 0.125 | 9 | 4.0 | 88 |
| EPTAM | 0.25 | — | — | 2** |
| EPTAM | 0.25 | 9 | 0.5 | 13 |
| EPTAM | 0.25 | 9 | 1.0 | 22 |
| EPTAM | 0.25 | 9 | 2.0 | 32 |
| EPTAM | 0.25 | 9 | 4.0 | 63 |
| EPTAM | 0.25 | 9 | 4.0 | 66 |
| EPTAM | 0.25 | — | — | 4* |
| EPTAM | 0.25 | 10 | 0.5 | 0 |
| EPTAM | 0.25 | 10 | 1.0 | 0 |
| EPTAM | 0.25 | 10 | 2.0 | 11 |
| EPTAM | 0.25 | 10 | 4.0 | 30 |
| EPTAM | 0.25 | — | — | 10* |
| EPTAM | 0.25 | 11 | 0.5 | 58 |
| EPTAM | 0.25 | 11 | 1.0 | 66 |
| EPTAM | 0.25 | 11 | 2.0 | 73 |
| EPTAM | 0.25 | 11 | 4.0 | 94 |

*Average of two trials.
**Average of four trials.

EXAMPLE 6

Non-herbicidal Activity of Extenders: Pre-plant Incorporation Test

This example offers herbicide test data for several representative extenders of the instant invention indicating their lack of herbicidal activity. The procedure employed for this test is the same as in Example 3 [B—Herbicide Tests] above except that the soil was not pretreated with either S-ethyl-N,N-di-n-propyl thiocarbamate or S-ethyl N,N-diisobutyl thiocarbamate, and the extenders were tested alone without being in composition with a thiocarbamate herbicide.

The results below in Table 5 indicate that the representative extenders are non-herbicidal when pre-plant incorporated (PPI) at 4 lb/acre.

carrier volume is 80 gallons/acre (748 L/ha) and a 4 lbs/acre rate (4.48 kg/ha) is used.

Twelve to fourteen days after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table 5.

TABLE 6

| Treatment Extender Compound No. | Non-Herbicidal Activity - PES | | | | | | | | Average % Weed Control |
|---|---|---|---|---|---|---|---|---|---|
| | FT | WG | WO | AMG | VL | MD | CD | YNS | |
| 1 | 20 | 10 | 0 | 0 | 0 | 0 | 0 | 0 | 4 |
| 2 | 0 | 0 | 0 | 0 | 0 | 0 | 0 | 0 | 0 |
| 3 | 0 | 0 | 0 | 0 | 0 | 0 | 0 | 0 | 0 |
| 4 | 0 | 0 | 0 | 0 | 0 | 0 | 0 | 0 | 0 |
| 5 | 0 | 0 | 0 | 0 | 0 | 0 | 0 | 0 | 0 |
| 6 | 0 | 0 | 0 | 0 | 0 | 0 | 0 | 0 | 0 |
| 7 | 0 | 0 | 0 | 0 | 0 | 0 | 0 | 0 | 0 |
| 8 | 0 | 0 | 0 | 0 | 0 | 0 | 0 | 0 | 0 |
| 9 | — | 0 | 0 | 0 | 0 | 0 | 0 | 0 | 0 |
| 10 | 60 | 85 | 20 | 10 | 20 | 0 | 0 | 0 | 24 |

TABLE 5

| | Nonherbicidal Activity - PPI | | | | | |
|---|---|---|---|---|---|---|
| Extender: Application Rate: | Keyed to Table 1 by Compound No. 4 lb/Acre | | | | | |
| Treatment Extender Compound No. | Milo | WG | WO | SHC | WG | Average % Weed Control |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 11 | 0 | 0 | 0 | 0 | 0 | 0 |

EXAMPLE 7

Non-Herbicidal Activity of Extenders: Pre-Emergence Herbicide Test

This example offers further data indicating that the representative extenders of the instant invention have no or insignificant herbicidal activity. The soil as in Example 6 was not previously treated with a thiocarbamate herbicide. The procedure used in these pre-emergence herbicide (PES) tests are as follows.

Herbicidal Screening Tests

On the dat preceding treatment, seed of eight different grass and broadleaf weed species are planted in loamy sand soil in individual rows in 6×10×3 inch flats. The seeds used are green foxtail (FT) (*Setaria viridis*), watergrass (WG) (*Echinochloa crus-galli*), wild oat (WO) (*Avena fatua*), annual moningglory (AMG) (*Ipomoea purpurea*), velvetleaf (VL) (*Abutilon theophrasti*), Indian mustard (MD) (*Brassica kaber*), curly dock (CD) (*Rumex crispus*) and yellow nutsedge (YNS) (*Cyperus esculentus*).

The flats are placed in the greenhouse, watered daily (both before and after chemical treatment) with a sprinkler and maintained at about 78° F. Chemical spray treatment is prepared by weighing out 333 mg of compound and dissolving in 25 ml acetone containing 1% polyoxyethylene sorbitan monolaurate emulsifier. From this stock solution 18 ml are removed and brought up to a 40 ml volume with a 19:1 water/acetone mixture. The

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier. Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock. Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene esters with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with macroscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. INJECTION WITH ANHYDROUS AMMONIA

The herbicidal compositions of the instant invention comprising a thiocarbamate herbicide, a mono-, di- or trihaloalkylphosphonodithioate extender and optionally an antidote can be applied to the soil by in-line injection with anhydrous ammonia. For pre-emergence soil injection applications of anhydrous ammonia, on conservation or conventional tilled acreage, the herbicidal compositions of the instant invention can be introduced into the anhydrous line using a metering pump which offers a constant rate of the output per acre independent of the anhydrous ammonia output rate. The herbicidal compositions' discharge hose can tee into the ammonia discharge line between the meter and the manifold. Injection depth can be from 4 to 5 inches. The herbicidal compositions can also be injected with anhydrous ammonia in no-till situations.

Other herbicide products can be surface applied and incorporated at the same time the herbicidal compositions of the instant invention and anhydrous ammonia are injected, or post-emergent applications can be used.

F. IN GENERAL

Each of the above formulations can be prepared as a package containing both the herbicide and the extender together with the other ingredients of the formulation (diluents, emulsifiers, surfactants, etc.). The formulations can also be prepared by a tank mix method, in which the ingredients are obtained separately and combined at the grower site. The herbicide and extender may both be used in the same type of formulation or a different formulation may be used for each, e.g. the herbicide may be in microcapsule form while the extender may be an emulsifiable concentrate, or vice versa.

As a further alternative, the herbicide and extender can be applied sequentially, with either being applied first. This is a less preferred method, however, since more effective results are obtained with simultaneous application.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide/extender compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide/extender composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A compound having the formula

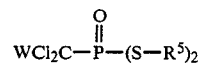

in which W is chlorine and $R^5$ is $C_1$–$C_6$ alkyl or $C_2$–$C_4$ alkenyl.

2. A compound according to claim 1 wherein $R^5$ is n-propyl, n-butyl or allyl.

* * * * *